(12) United States Patent
Reimer et al.

(10) Patent No.: US 7,791,794 B2
(45) Date of Patent: Sep. 7, 2010

(54) SURGICAL MICROSCOPE HAVING AN OCT-SYSTEM

(75) Inventors: Peter Reimer, Ellwangen (DE); Christoph Hauger, Aalen (DE); Alfons Abele, Schwäbisch Gmünd (DE); Markus Seesselberg, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 412 days.

(21) Appl. No.: 11/984,818

(22) Filed: Nov. 21, 2007

(65) Prior Publication Data

US 2008/0304144 A1    Dec. 11, 2008

(30) Foreign Application Priority Data

Apr. 24, 2007    (DE) .................... 10 2007 019 679

(51) Int. Cl.
*G02B 21/00* (2006.01)
(52) U.S. Cl. .................... 359/380; 359/368; 359/372
(58) Field of Classification Search .......... 359/368–390
See application file for complete search history.

(56) References Cited

U.S. PATENT DOCUMENTS 5,321,501 A    6/1994   Swanson et al.
5,795,295 A    8/1998   Hellmuth et al.
6,004,314 A *  12/1999  Wei et al. .................... 606/12
2008/0204655 A1* 8/2008  Kikawa et al. .............. 351/206
2010/0033676 A1* 2/2010  De Vries et al. ............. 351/206

FOREIGN PATENT DOCUMENTS

| DE | 10 2004 049 368 | 4/2006 |
|----|-----------------|--------|
| DE | 10 2005 005 568 | 8/2006 |
| EP | 1 220 004       | 7/2002 |
| EP | 1 231 496       | 8/2002 |
| WO | WO 2006/100544  | 9/2006 |

OTHER PUBLICATIONS

Expanded European Search Report (Translation into English).

* cited by examiner

*Primary Examiner*—Thong Nguyen
(74) *Attorney, Agent, or Firm*—Walter Ottesen

(57) ABSTRACT

A surgical microscope (100) has viewing beams (109a, 109b) passing through a microscope imaging optic which includes a microscope main objective system (101) having a magnification system of variable magnification. The microscope imaging optic transposes a convergent viewing beam (109a, 109b) from the object region (114) into a parallel beam. The surgical microscope includes an OCT-system (120) for examining the object region (114). The OCT-system (120) makes available an OCT-scanning beam (190) which is guided through the microscope imaging optic.

17 Claims, 3 Drawing Sheets

SURGICAL MICROSCOPE HAVING AN OCT-SYSTEM

CROSS REFERENCE TO RELATED APPLICATION

This application claims priority of German patent application No. 10 2007 019 679.4, filed Apr. 24, 2007, the entire content of which is incorporated herein by reference.

FIELD OF THE INVENTION

The invention relates to a surgical microscope having a microscope imaging optic which includes a microscope main objective system as well as a magnification system having variable magnification. The surgical microscope further has a viewing beam path which passes through the microscope imaging optic. The microscope imaging optic transposes a convergent viewing beam from the object region into a beam having parallel rays. An OCT-system is provided for examining the object region.

BACKGROUND OF THE INVENTION

A surgical microscope of the kind described above is known from U.S. Pat. No. 5,795,295. Here, a surgical microscope is described having a microscope main objective through which a stereoscopic viewing beam path passes. A zoom system for variable magnification is assigned to the microscope main objective. The surgical microscope contains an OCT-system. This OCT-system includes a component assembly for generating an OCT-scanning beam of short coherent laser radiation and further includes an analyzer unit for evaluating interference signals. A unit for scanning the OCT-scanning beam is assigned to this component assembly. The unit for scanning contains two scan mirrors, which can be displaced about two movement axes, in order to scan a surgical region with the OCT-scanning beam. In the surgical microscope in U.S. Pat. No. 5,795,295, the OCT-scanning beam is coupled into the illuminating beam path of the surgical microscope via a divider mirror and, with this illuminating beam path, the OCT-scanning beam is directed through the microscope main objective.

A non-invasive examination and measurement of the structures within a biological tissue are made possible by the method of the optical coherence tomography (OCT). As an image providing process, the optical coherence tomography permits especially section images or volume images of biological tissue to be generated with micrometer resolution. A corresponding OCT-system includes a source for time-dependent incoherent and spatially coherent light having a specific coherence length which is guided to a specimen beam path and a reference beam path. The specimen beam path is directed onto the tissue to be examined. Laser radiation, which is radiated back into the specimen beam path because of scatter centers in the tissue, superposes the OCT-system with laser radiation from the reference beam path. An interference signal develops because of the superposition. The position of the scatter centers for the laser radiation in the examined tissue can be determined from this interference signal.

For OCT-systems, the building principles of the "time-domain OCT" and of the "Fourier-domain OCT" are known.

The configuration of a "time-domain OCT" is described, for example, in U.S. Pat. No. 5,321,501 with reference to FIG. 1a at column 5, line 40, to column 11, line 10. In a system of this kind, the optical path length of the reference beam path is continuously varied via a rapidly moving reference mirror. The light from specimen beam path and reference beam path is superposed on a photo detector. When the optical path lengths of the specimen and reference beam paths are coincident, then an interference signal is provided on the photo detector.

A "Fourier-domain OCT" is, for example, described in international patent publication WO 2006/100544 A1. To measure the optical path length of a specimen beam path, light from the specimen beam path is superposed onto light from a reference beam path. In contrast to the time-domain OCT, the light from the specimen beam path and reference beam path is not supplied directly to a detector for a measurement of the optical path length of the specimen beam path but is first spectrally dispersed by means of a spectrometer. The spectral intensity of the superposed signal generated in this manner from specimen beam path and reference beam path is then detected by a detector. By evaluating the detector signal, the optical path length of the specimen beam path can be determined.

U.S. patent publication US 2002/118449 A1 discloses a surgical microscope which permits a viewing person to examine a surgical region with a stereoscopic viewing beam path by looking into an ocular. The surgical microscope contains a unit for reflecting in data with a display and a beam splitter configured as a divider cube. This beam splitter is mounted in the base body of the surgical microscope in the parallel viewing beam path between the microscope main objective and the ocular. The beam splitter superposes a display image onto the parallel viewing beam in the surgical microscope. The display image is imaged at infinity with a display optic.

SUMMARY OF THE INVENTION

It is an object of the invention to provide a compactly configured surgical microscope having variable magnification wherein the detection of depth images of an object region is possible with an OCT-scanning beam path. The course of the OCT-scanning beam corresponds to the course of the optical viewing beam in the surgical microscope which effects a magnified image of the object region in the ocular for a viewing person. In the object region, the cross section of the OCT-scanning beam adapts to the selected magnification.

The surgical microscope of the invention is for defining a viewing beam path and includes: an imaging optic assembly mounted so as to permit the viewing beam path to pass therethrough permitting examination of a region of an object; the imaging optic assembly including a microscope main objective assembly mounted so as to permit the viewing beam path to pass therethrough; the imaging optic assembly, further including a magnification assembly having a variable magnification and being mounted in the viewing beam path upstream of the microscope main objective assembly; the imaging optic assembly being adapted to transpose a convergent viewing beam from the object region into a viewing beam having parallel rays; an OCT-system for examining the object region; and, the OCT-system providing an OCT-scanning beam guided through the imaging optic assembly.

In this way, it is ensured, especially for an uneven object region, that the optical viewing beam and the OCT-scanning beam cover identical zones of the object region. In this way, by means of the OCT-scanning beam, precisely the viewing image can be scanned which is present for the viewing person in the ocular. Depth sections of the object region are detected which are based on the OCT-scanning beam.

According to a further embodiment of the invention, an in-coupling element is provided which couples the OCT-scanning beam into the viewing beam in order to guide the OCT-scanning beam superposed on the viewing beam through the microscope imaging optic to the object region. Preferably, the in-coupling element is configured as a divider mirror, especially as a planar mirror or a divider cube. In this way, a secondary viewer can always have a clear view to the object region.

According to another feature of the invention, an out-coupling element is mounted between the microscope imaging optic and the in-coupling element in order to couple out image information from the viewing beam path.

In another embodiment of the invention, an afocal lens system is mounted between the in-coupling element and the microscope main objective system. The afocal lens system is preferably configured as a zoom system. In this way, it is possible to vary the lateral resolution of the OCT-data, which is obtainable with the OCT-system, matched to the viewing image which is seen by a viewing person in the ocular of the surgical microscope.

In another embodiment of the invention, the OCT-system includes a first scan mirror for scanning the OCT-scanning beam. Preferably, in addition, a second scan mirror is provided. The first scan mirror can be moved about a first rotational axis and the second scan mirror can be moved about a second rotational axis. The first and second rotational axes are laterally offset and at right angles to each other. In this way, a scanning of the object region in accordance with a perpendicularly-running raster pattern is possible.

According to another feature of the invention, the OCT-system includes a light conductor which has a light exit section for the OCT-scanning beam. Means for moving the light exit section of the light conductor are provided. In this way, an OCT-scanning plane can be varied in the object region and it is possible to adjust the system for different OCT-wavelengths while considering the optical components in the viewing beam path for secondary viewing. The optical components are designed for visible light.

According to another feature of the invention, an adjustable optical system is provided in the OCT-scanning beam path for the adjustment of a geometric image of the exit end of the light conductor into an OCT-scanning plane. In this way, the OCT-scanning plane of the surgical microscope can be shifted relative to the viewing plane of the optical viewing beams of the system and it is possible, when adjusting the imaging scale for the microscope imaging optic, to so readjust the imaging scale for the OCT-scanning radiation that the imaging scale in the optical viewing beam corresponds to the imaging scale in the OCT-scanning beam. Preferably, the particular imaging scales can be maintained to be identical.

According to another feature of the invention, a drive unit is assigned to the adjustable optical element. In this way, for example, the OCT-scanning plane can be varied by a pregiven amount relative to the viewing plane of the surgical microscope.

According to another feature of the invention, the OCT-system is designed for making available a first OCT-scanning light beam having a first wavelength and for making available a second OCT-scanning light beam having a second wavelength different from the first wavelength. In this way, the surgical microscope can be optimized for the examination of different tissue structures and body organs of a patient.

In a further embodiment of the invention, a first OCT-system and a second OCT-system are provided which make available OCT-scanning light beams of different wavelengths. In this way, an examination of an object region is possible on the basis of different OCT-wavelengths with maximum resolution. Especially, tissue at different penetration depths can be examined with OCT-scanning light beams. Furthermore, it is possible to design the surgical microscope for different applications.

According to another feature of the invention, a coupling of the microscope imaging optic and an OCT-system is provided in order to adjust a corresponding change of the optical path length in the OCT-system when there is a change of the work distance of the surgical microscope. In this way, it is ensured that an object region, which is sharply imaged by the microscope imaging optic, can be scanned also with the OCT-system.

According to a further feature of the invention, a coupling of the microscope imaging optic and the collimation optic of an OCT-system is provided in order to adapt the imaging scale in the optical viewing beam path and the imaging scale in the OCT-scanning beam path to each other. In this way, it is ensured that the OCT-scanning beam scans the viewing region visible in the optical viewing beam paths.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
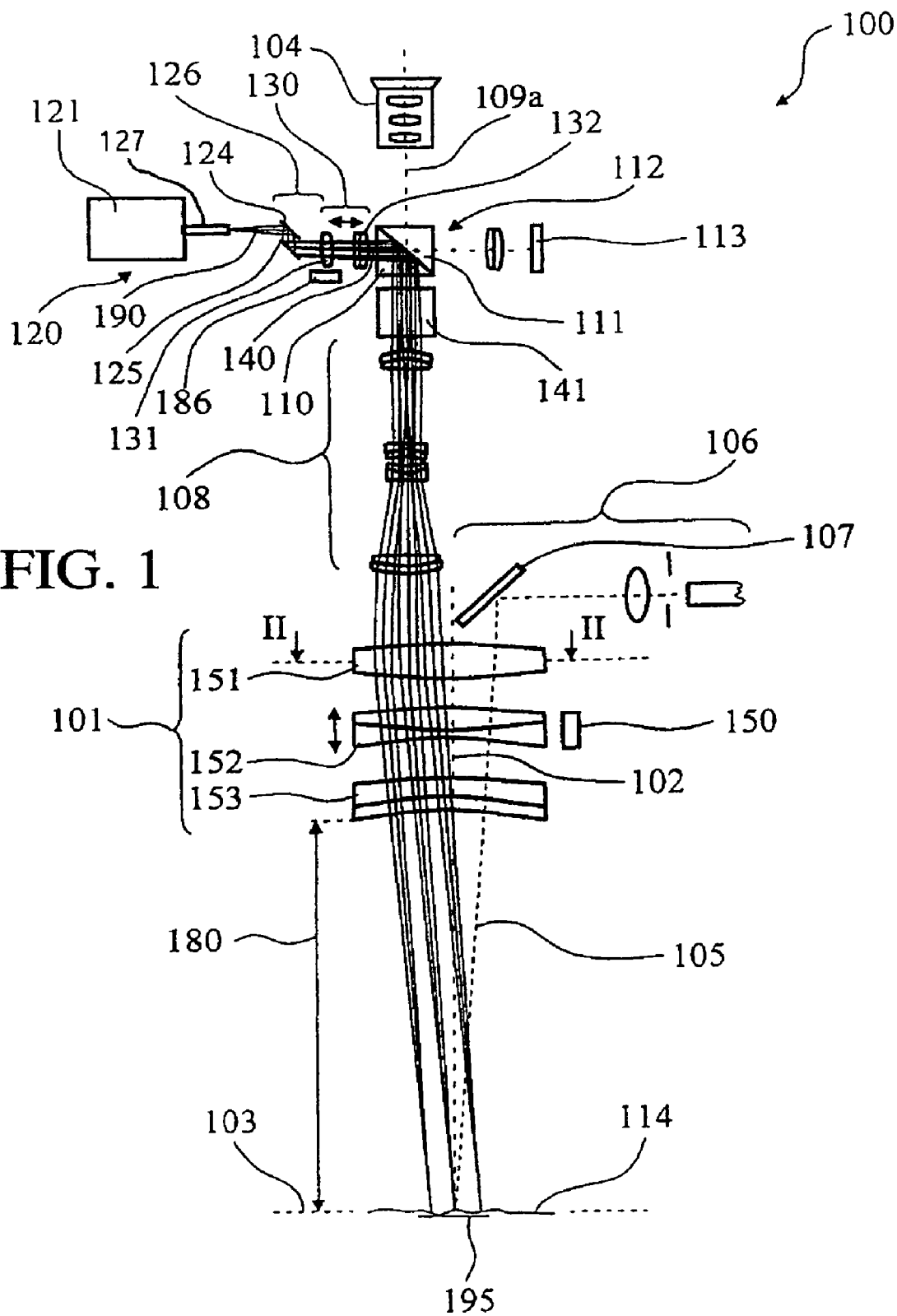
FIG. 1 shows a first surgical microscope having an integrated OCT-system.

The surgical microscope 100 in FIG. 1 has a microscope main objective system 101 defining an optical axis 102 and a corresponding shiftable focal plane 103. The microscope main objective system 101 can be focused via a position drive 150. The microscope main objective system 101 includes component optics (151, 152, 153). Stereoscopic viewing beam paths of a binocular tube 104 and the illuminating beam 105 of an illuminating device 106 having an illuminating mirror 107 pass through the microscope main objective system. This illuminating mirror 107 is arranged on the side of the microscope main objective system 101 facing away from the object.

A zoomable magnification system 108 is assigned to the binocular tube 104. The microscope main objective system 101 and the zoomable magnification system 108 conjointly define the microscope imaging optic of the surgical microscope 100. FIG. 1 shows a right hand viewing beam path 109a of the stereoscopic viewing beam path in the surgical microscope 100.

A first divider cube 112 is disposed in the parallel, right hand viewing beam path 109a between the binocular tube 104 and the zoomable magnification system 108. The first divider cube 112 is made up of right angle prisms (110, 111). A divider cube, which is identical to the first divider cube 112, is mounted at the corresponding position in the parallel, left hand viewing beam path. The first divider cube 112 and the second divider cube have a double function, namely, they operate as in-coupling elements to couple the display of a first display 113 and the display of a second display (not shown in FIG. 1) into the right hand viewing beam path 109a and into the left hand viewing beam path of the surgical microscope.

In this way, the display of the first display 113 and the display of the second display are superposed on the image of object region 114 in the binocular tube 104. At the same time, the first divider cube and the second divider cube function as elements for coupling in an OCT-scanning beam 190 provided by a first OCT-system 120.

The surgical microscope 100 includes the first OCT-system 120 for recording OCT-images. The OCT-system includes a unit 121 for generating and analyzing an OCT-scanning beam 190 which exits from a light conductor 127. The scanning beam 190, which exits from the light conductor 127, is guided to a first scan mirror 124 and a second scan mirror 125 of an OCT-scanning unit 126. After the OCT-scanning unit 126, the scanning beam 190 passes through an adjustable collimation optic 130 having a lens 131 and a lens 132. The collimation optic 130 has a drive 186 and bundles the scanning beam rays 190 to a beam 140 having parallel rays.

It is also possible to deflect a parallel OCT-scanning beam with the first scan mirror 124 and the second scan mirror 125 of the OCT-scanning unit 126. For this purpose, a suitable collimation optic is needed, for example, a converging lens which is disposed between light conductor 127 and the OCT-scanning unit 126. A collimation optic 130, which is disposed on the side of the OCT-scanning unit 126 facing away from the light conductor, is then not necessary.

The beam 140 from the OCT-scanning unit 126 is guided to the divider cube 112 in the viewing beam path 109a. The divider cube 112 is essentially transparent for the spectral range of viewing light in this viewing beam path visible to humans. The divider cube 112, however, reflects the OCT-scanning beam and superposes the latter onto the viewing beam 109a. It is noted that the divider cube 112 can also be configured as a mirror element having a planar plate.

The light of the OCT-scanning beam 190 is bundled by the microscope main objective system 101 in an OCT-scanning plane 195. The OCT-scanning plane 195 is the plane of the geometric image of the exit end of the light conductor 127 in the object region. This geometric image is determined by the optical elements in the OCT-scanning beam path with the OCT-scanning unit 126, collimation optic 130, divider cube 112 and microscope main objective system 101. That is, the corresponding geometric image of the light conductor exit end lies in the OCT-scanning plane 195.

The light backscattered into the OCT-scanning beam path arrives back in the unit 121 via the following: the microscope main objective system 101; the zoomable magnification system 108; and, the divider cube 112. In the unit 121, the OCT-scanning light, which is backscattered from the object region 114, interferes with OCT-radiation from a reference beam path. The interference signal is detected by a detector and is evaluated by a computer unit which determines from this signal an optical path length difference between scatter centers for OCT-light in the object region 114 and the path length of light in the reference branch.

With a variation of the work distance 180 of the surgical microscope 100 because of a shift of the microscope main objective system 101, the optical path lengths of the scanning beam paths from the respective OCT-systems in the surgical microscope also change. The position drive 150 of the focusable microscope main objective system 101 is therefore electrically connected to the OCT-systems in the surgical microscope via a signal line (not shown). This effects a coupling of the OCT-systems to the microscope main objective system in order to correspondingly adapt the optical path lengths of the reference paths in the OCT-systems as required in the case of a variation of the surgical microscope work distance 180 from the object region 114.

An out-coupling element 141 is disposed between the zoomable magnification system 108 and the divider cube 112 in order to supply image information from the object region 114 to a documentation unit (not shown).

Figure 2:
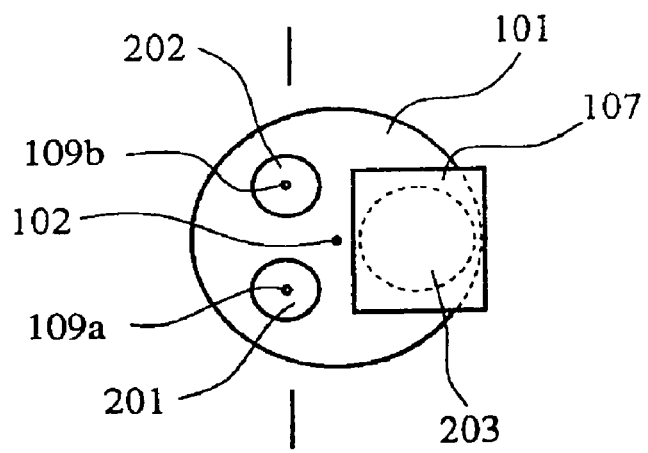
FIG. 2 is a section view taken along line II-II of FIG. 1 through the microscope main objective in the surgical microscope of FIG. 1.

FIG. 2 is a section view taken along line II-II of FIG. 1. FIG. 2 explains the course of the stereoscopic viewing beam paths in the surgical microscope 100 of FIG. 1. The optical axis 102 of the microscope main objective system 101 lies in the center of the main objective system 101. The right viewing beam path 109a and the left viewing beam path 109b pass through microscope main objective system 101 together with the illumination beam path 105, which is deflected by illumination mirror 107, in respective sections (201, 202, 203) separated from each other.

Figure 3:
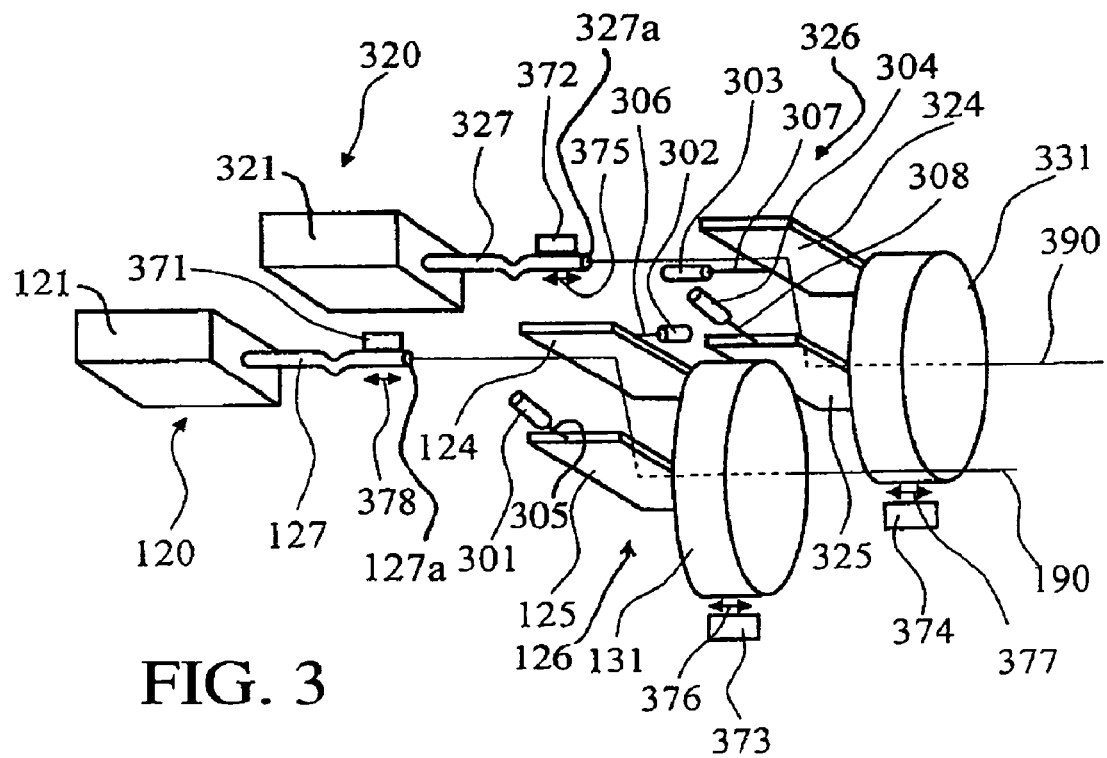
FIG. 3 is a detail view of the surgical microscope having first and second OCT-systems.

FIG. 3 shows the first OCT-system 120 and the second OCT-system 320 in the surgical microscope 100 of FIG. 1. In the same manner as the first OCT-system 120, the second OCT-system 320 includes a unit 321 for generating and analyzing an OCT-scanning beam. The wavelength ranges of the OCT-scanning beams of the two OCT-systems (120, 320) are, however, different. The first OCT-system is based on an OCT-scanning beam having the wavelength $\lambda_1$=1310 nm. The second OCT-system 320 operates with an OCT-scanning beam of the wavelength $\lambda_2$=800 nm. It is understood that the OCT-systems can also be designed for other operating wavelengths. Operating wavelengths are advantageously realized especially in the range of 600 nm<$\lambda$<1500 nm and are advantageous depending upon application.

The OCT-scanning beam 190 of the first OCT-system 120 is coupled via the collimation optic 130 and the first divider cube into the right viewing beam path of the surgical microscope 100. The OCT-scanning beam 390 of the second OCT-system 320 is superposed via a second collimation optic and the second divider cube into the left viewing beam path of the surgical microscope 100.

As with the OCT-system 120, the OCT-system 320 includes an OCT-scanning unit 326 having scan mirrors (324, 325) and a converging lens 331 which collects the OCT-scanning beam 390 to a beam having parallel rays.

The first scan mirrors (124, 324) and the second scan mirrors (125, 325) of the OCT-systems (120, 320) are mounted so as to be rotationally movable about two axes (305, 306, 307, 308) by means of position drives (301, 302, 303, 304) with the axes being perpendicular to each other. In this way, the OCT-scanning beams (190, 390) can be scanned independently of each other over a plane.

In order to make possible the adjustment of the OCT-scanning planes with respect to the object plane of the optical viewing beam paths in the surgical microscope 100 of FIG. 1 by a person, a displaceability of the converging lenses (131, 331) and the exit ends (127a, 327a) of the light conductors (127, 327) is provided. For this purpose, respective drive units (371, 372, 373, 374) are assigned to the converging lenses (131, 331) and the light conductors (127, 327). The converging lenses (131, 331) and the light conductors (127, 327) can be displaced in correspondence to the double arrows (376, 377, 378, 375) by means of these drive units. In this way, not only the position of the OCT-scanning plane can be varied but also a magnification or demagnification of the exit ends of the light conductors (127, 327) can be adjusted to desired values.

Figure 4:
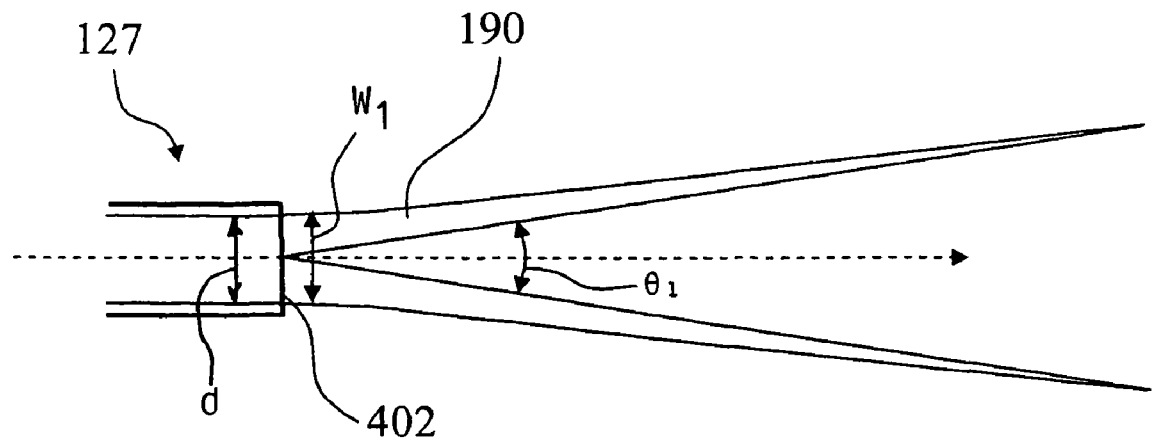
FIG. 4 shows the intensity distribution of the OCT-scanning beam exiting from the light conductor of an OCT-system in the surgical microscope; and, FIG. 5 shows the intensity distribution of the OCT-scanning beam in the OCT-scanning plane in the object region of the surgical microscope.

FIG. 4 shows a front portion of the light conductor 127 of FIG. 1 having front face 402. The light conductor 127 operates as a monomode fiber for light of the wavelength $\lambda_1=1310$ nm. The diameter (d) of the fiber core of the light conductor 127 satisfies the relationship:

$$\frac{d}{2} < 2.4 \frac{\lambda_1}{2\pi NA},$$

wherein: NA is the numerical aperture of the front face of the light conductor. Preferably, the diameter (d) of the fiber core of the light conductor 127 lies in the range of 5 µm<d<10 µm. In this parameter range, the light conductor 127 conducts the light with a Gaussian-shaped wave mode. The OCT-scanning light beam 190 exits from the light conductor 127 with an approximately Gaussian-shaped beam profile which is characterized by a waist parameter $W_1$ and an aperture parameter $\theta_1$ wherein:

$$\theta_1 = \frac{\lambda}{\pi W_1}$$

An aperture angle of $\theta_1=0.0827$ rad results thereby as an index for the beam divergence for a fiber core diameter of $d_1=10$ µm and a wavelength $\lambda_1=1310$ nm.

The front face 402 of the light conductor 127 is imaged on the object region 114 in the OCT-scanning plane 195 via the following: the scan mirrors 124 and 125 in the surgical microscope 100 of FIG. 1; the collimation optic 130; the divider cube 112; the magnification system 108; and, the microscope main objective system 101.

Figure 5:
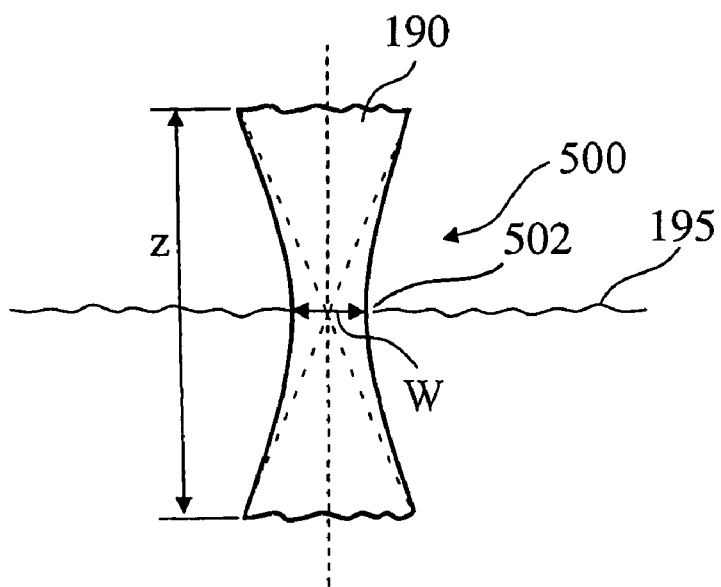

FIG. 5 shows the course of the intensity distribution of the OCT-scanning light beam 190 perpendicular to the OCT-scanning plane 195. In the OCT-scanning plane 195, the intensity distribution of the OCT-scanning radiation has a smallest constriction. The diameter of the OCT-scanning beam path increases outside of the OCT-scanning plane. The OCT-scanning light beam 190 exits from the light conductor 127 of FIG. 4 with an approximately Gaussian-shaped beam profile. For this reason, the collimation optic 130 and the microscope main objective system 101 effect a so-called Gaussian bundle 500 of the OCT-scanning light beam 190 in the region of the OCT-scanning plane 195. This Gaussian bundle 500 is characterized by the confocal parameter (z) as an index for the longitudinal expansion of the constriction of the Gaussian bundle and by the waist parameter W as an index for the diameter of the smallest constriction 502 of the OCT-scanning light beam 190, that is, for the diameter of the constriction thereof. The following applies:

$$z = 2 \frac{W^2 \pi}{\lambda_1},$$

wherein: $\lambda_1$ is the wavelength of the OCT-scanning light beam. The following relationship applies between the waist parameter W of the Gaussian bundle 500 and the waist parameter $W_1$ of the scanning light beam 190 (FIG. 4) which exits from the light conductor 127:

W=βW₁, wherein: β is the magnification parameter or demagnification parameter of the above-mentioned geometric image of the exit end of light conductor 127 of FIG. 1 in the OCT-scanning plane. The parameter β is coupled to the focal length $f_1$ of the collimation optic 130 of FIG. 1 and the focal length $f_2$ of the microscope imaging optic having microscope main objective system 101 and magnification system 108 via the following relationship:

$$\frac{f_2}{f_1} = \beta$$

The displaceable collimation optic of the OCT-systems makes possible to adapt imaging parameters β for the corresponding OCT-beam paths to a change of the imaging scale of the microscope imaging optic. Preferably, the imaging scales are selected to be the same for this purpose.

For a specific scanning pattern of the OCT-scanning beam, this effects that the pattern adapts automatically to the viewing image which is seen by a viewing person in the ocular of the surgical microscope 100 of FIG. 1.

The size of structures, which can be resolved with the OCT-scanning light beam 190, is determined by the diameter of the beam 190 in the OCT-scanning plane 195, that is, by the waist parameter W. If, for example, an application requires a lateral resolution of the OCT-system in the surgical microscope of approximately 40 µm, then, according to the Nyquist theorem, the cross section of the OCT-scanning light beam 190 must amount to approximately 20 µm on the surface. For a given wavelength µ for the OCT-scanning light beam 190 of FIG. 1, the magnification of the optical image in the OCT-beam path and the diameter of the fiber core in the light conductor 127 must be suitably selected for a desired resolution of the OCT-system 120.

The confocal parameter (z) as an index for the longitudinal expansion of the waist of the Gaussian bundle determines the axial depth of field from which backscattered light can be detected in the OCT-scanning beam path 190 of FIG. 1. The smaller the confocal parameter (z), the greater is the loss of the OCT-system with respect to lateral resolution when removing an object from the OCT-scanning plane 195 with this object having been scanned with the OCT-scanning beam. The reason for this is that the location of the scatter centers can be localized only within the "funnel" defined by the waist parameter W and the confocal parameter (z).

As the axial resolution of an OCT-system is delimited on the one hand by the specific coherence length of the light of the light source utilized in the OCT-system and, on the other hand, the lateral resolution of the OCT-system decreases when the depth index thereof exceeds the expansion given by the confocal parameter (z), the adjustment of the confocal parameter (z) to the depth index of the OCT-system is favorable. The depth index is a measuring range within which scattering centers in the object can be measured in the z-direction.

For a specific wavelength λ of the OCT-scanning light beam 190, the possible lateral resolution of the OCT-system of FIG. 1 results because the wavelength λ and confocal parameter (z) determine the waist parameter W. The optical units in the OCT-scanning beam path 190 of FIG. 1 and the dimensioning of the fiber core of the light conductor 127 are then to be selected so that the particular waist parameter W results. The same applies to the optical units in the OCT-scanning beam of the second OCT-system 320 in the surgical microscope.

The surgical microscope 100 is so designed that the focal plane 103 of the microscope main objective 101 for the visible spectral region and the OCT-scanning plane 195 are coincident. Then, the waist 502 of the OCT-scanning light beam shown in FIG. 5 lies in the focal plane of the surgical microscope.

Alternative to this design of the surgical microscope, an offset of the OCT-scanning plane and the focal plane of the surgical microscope can be provided. Preferably, this offset is not greater than the confocal parameter (z) of the OCT-scanning light beam in the region of the OCT-scanning plane. This makes it possible, for example, to visualize an object region utilizing OCT with this object region lying directly below the focal plane of the surgical microscope. However, it can also be purposeful to provide for a specific application a defined offset which exceeds the confocal parameter in order, for example, to examine the front side of the cornea of the eye of a patient with the surgical microscope and, at the same time, to visualize the rear side of the cornea of the patient eye or the lens thereof by means of the OCT-system.

The measurement depth index for the OCT-system can be maximized in the object region in that the OCT-scanning plane is disposed by the confocal parameter (z) further from the microscope main objective system 101 of FIG. 1.

It is understood that the foregoing description is that of the preferred embodiments of the invention and that various changes and modifications may be made thereto without departing from the spirit and scope of the invention as defined in the appended claims.

What is claimed is:

1. A surgical microscope defining a viewing beam path and comprising:
    an imaging optic assembly mounted so as to permit said viewing beam path to pass therethrough permitting examination of a region of an object;
    said imaging optic assembly including a microscope main objective assembly mounted so as to permit said viewing beam path to pass therethrough;
    said imaging optic assembly further including a magnification assembly having a variable magnification and being mounted in said viewing beam path upstream of said microscope main objective assembly;
    said imaging optic assembly being adapted to transpose a convergent viewing beam from said object region into a viewing beam having parallel rays;
    an OCT-system for examining said object region; and,
    said OCT-system providing an OCT-scanning beam guided through said imaging optic assembly.

2. The surgical microscope of claim 1, further comprising an in-coupling element for coupling said OCT-scanning beam into said viewing beam path to permit said OCT-scanning beam to be guided to said region of said object superposed on said viewing beam path.

3. The surgical microscope of claim 2, further comprising a display for displaying information; and, said in-coupling element being mounted to receive said information for coupling said information into said viewing beam path.

4. The surgical microscope of claim 2, wherein said in-coupling element is a divider mirror.

5. The surgical microscope of claim 4, wherein said divider mirror is a planar mirror.

6. The surgical microscope of claim 2, wherein said in-coupling element is a divider cube.

7. The surgical microscope of claim 2, further comprising an out-coupling element for coupling image information out of said viewing beam path; and, said out-coupling element being arranged between said imaging optic assembly and said in-coupling element.

8. The surgical microscope of claim 2, wherein said OCT-system comprises a collimating optic for bundling the rays of said OCT-scanning beam into essentially parallel rays supplied to said in-coupling element.

9. The surgical microscope of claim 1, wherein said magnification assembly is an afocal lens assembly.

10. The surgical microscope of claim 9, wherein said afocal lens assembly is a zoom assembly.

11. The surgical microscope of claim 1, wherein said OCT-system further comprises a first scan mirror for scanning said OCT-scanning beam; and, a first device for rotating said first scan mirror about a first rotational axis.

12. The surgical microscope of claim 11, wherein said OCT-system further comprises a second scan mirror for scanning said OCT-scanning beam; and, a second device for rotating said second scan mirror about a second rotational axis laterally offset at a right angle to said first rotational axis.

13. The surgical microscope of claim 1, wherein said OCT-system further comprises a light conductor having an end portion having a light exit end face for said OCT-scanning beam; and, means for moving said end portion.

14. The surgical microscope of claim 1, wherein said OCT-system further comprises:
    a light conductor having an end portion having a light exit end face for said OCT-scanning beam;
    an adjustable optic assembly arranged in said OCT-scanning beam for imaging said light exit end face into an OCT-scanning plane.

15. The surgical microscope of claim 14, wherein said OCT-system further comprises a drive unit for displacing said adjustable optic assembly.

16. The surgical microscope of claim 1, wherein said OCT-scanning beam is a first OCT-scanning beam; said OCT-system provides a second OCT-scanning beam; and, said first OCT-scanning beam has a first wavelength and said second OCT-scanning beam has a second wavelength different from said first wavelength.

17. The surgical microscope of claim 1, wherein said OCT-system is a first OCT-system providing a first OCT-scanning beam and said surgical microscope further comprises a second OCT-system providing a second OCT-scanning beam; and, said first and second OCT-scanning beams have different wavelengths.

* * * * *

UNITED STATES PATENT AND TRADEMARK OFFICE
CERTIFICATE OF CORRECTION

PATENT NO. : 7,791,794 B2
APPLICATION NO. : 11/984818
DATED : September 7, 2010
INVENTOR(S) : Peter Reimer et al.

It is certified that error appears in the above-identified patent and that said Letters Patent is hereby corrected as shown below:

Column 7:
Line 24: delete "$\theta_1=0.0827$" and substitute -- $\theta_1 \approx 0.0827$ -- therefor.

Column 8:
Line 29: delete "$\mu$" and substitute -- $\lambda$ -- therefor.

Signed and Sealed this

Sixteenth Day of November, 2010

David J. Kappos
*Director of the United States Patent and Trademark Office*